(12) United States Patent
Bedford et al.

(10) Patent No.: US 12,292,074 B2
(45) Date of Patent: May 6, 2025

(54) LOCKING ASSEMBLY FOR A MEDICAL DEVICE

(71) Applicant: SomnoMed Limited, Crows Nest (AU)

(72) Inventors: Christopher Russell Bedford, Rozelle (AU); Joshua Luke Meier, Berowra (AU); Wataru Obuchi, Maroubra (AU); Harrison John Wood, Ourimbah (AU)

(73) Assignee: SomnoMed Limited, Crows Nest (AU)

( * ) Notice: Subject to any disclaimer, the term of this patent is extended or adjusted under 35 U.S.C. 154(b) by 123 days.

(21) Appl. No.: 17/596,267

(22) PCT Filed: Jun. 5, 2020

(86) PCT No.: PCT/AU2020/050579
§ 371 (c)(1),
(2) Date: Dec. 6, 2021

(87) PCT Pub. No.: WO2020/243793
PCT Pub. Date: Dec. 10, 2020

(65) Prior Publication Data
US 2022/0243755 A1      Aug. 4, 2022

(30) Foreign Application Priority Data

Jun. 7, 2019 (AU) ................................. 2019901984

(51) Int. Cl.
*F16B 35/06* (2006.01)
*F16B 33/00* (2006.01)
(Continued)

(52) U.S. Cl.
CPC ............ *F16B 35/06* (2013.01); *F16B 33/002* (2013.01); *A61C 7/36* (2013.01); *A61F 5/566* (2013.01)

(58) Field of Classification Search
CPC ........ F16B 23/00; F16B 33/002; F16B 35/06; F16B 37/14; F16B 39/08; F16B 39/10;
(Continued)

(56) References Cited

U.S. PATENT DOCUMENTS 915,068 A * 3/1909 Bowen .................... F16B 37/14
261/DIG. 38
2,363,665 A * 11/1944 George ................... F16B 37/14
411/921

(Continued)

FOREIGN PATENT DOCUMENTS

| GB | 2563876 A | 1/2019 |
|---|---|---|
| WO | 2019094744 A1 | 5/2019 |
| WO | 2020243793 A1 | 12/2020 |

OTHER PUBLICATIONS

International Search Report for App. No. PCT/AU2020/050579, dated Jul. 23, 2020, 4 pages.

*Primary Examiner* — Roberta S Delisle
(74) *Attorney, Agent, or Firm* — Butzel Long

(57) ABSTRACT

A locking assembly (10) for a medical device (1), the device (1) adapted to adjust the position of an upper teeth engagement member to a lower teeth engagement member, the device (1) having a plate, an elongate recess and a block slidable along said recess to adjust the position of the members relative to each other; the locking assembly (10) including: a screw having an elongate shaft having a thread extending substantially towards one end and a head at the other end, the thread adapted to engage the block, the head having at least one engagement member; and a cap having a corresponding at least one engagement member in use to lock the engagement members together to inhibit said screw from rotating in said block.

12 Claims, 6 Drawing Sheets

(51) Int. Cl.
*A61C 7/36* (2006.01)
*A61F 5/56* (2006.01)

(58) Field of Classification Search
CPC . F16B 39/24; A61C 7/36; A61F 5/566; Y10S 411/91
USPC .......... 411/116, 117–118, 372.5–372.6, 373, 411/376, 383
See application file for complete search history.

(56) References Cited

U.S. PATENT DOCUMENTS

| | | | |
|---|---|---|---|
| 4,613,265 A | 9/1986 | Jean-Claude | |
| 5,391,028 A * | 2/1995 | Charles | F16B 37/145 411/374 |
| 5,603,472 A * | 2/1997 | Hutter, III | F16B 35/06 411/910 |
| 6,302,630 B1 * | 10/2001 | Grant | F16B 35/06 411/510 |
| 6,517,301 B2 | 2/2003 | Hartmann | |
| 7,713,012 B2 * | 5/2010 | Coonjohn | B60R 13/005 411/372.6 |
| 2006/0196512 A1 | 9/2006 | Gaskell | |
| 2007/0189877 A1 * | 8/2007 | Wells | F16B 33/004 411/372.5 |
| 2007/0235037 A1 | 10/2007 | Thornton | |
| 2012/0234402 A1 * | 9/2012 | Richards | F16B 35/06 411/375 |
| 2013/0017034 A1 | 1/2013 | Chen | |
| 2022/0257409 A1 * | 8/2022 | Radmand | A61F 5/566 |

* cited by examiner

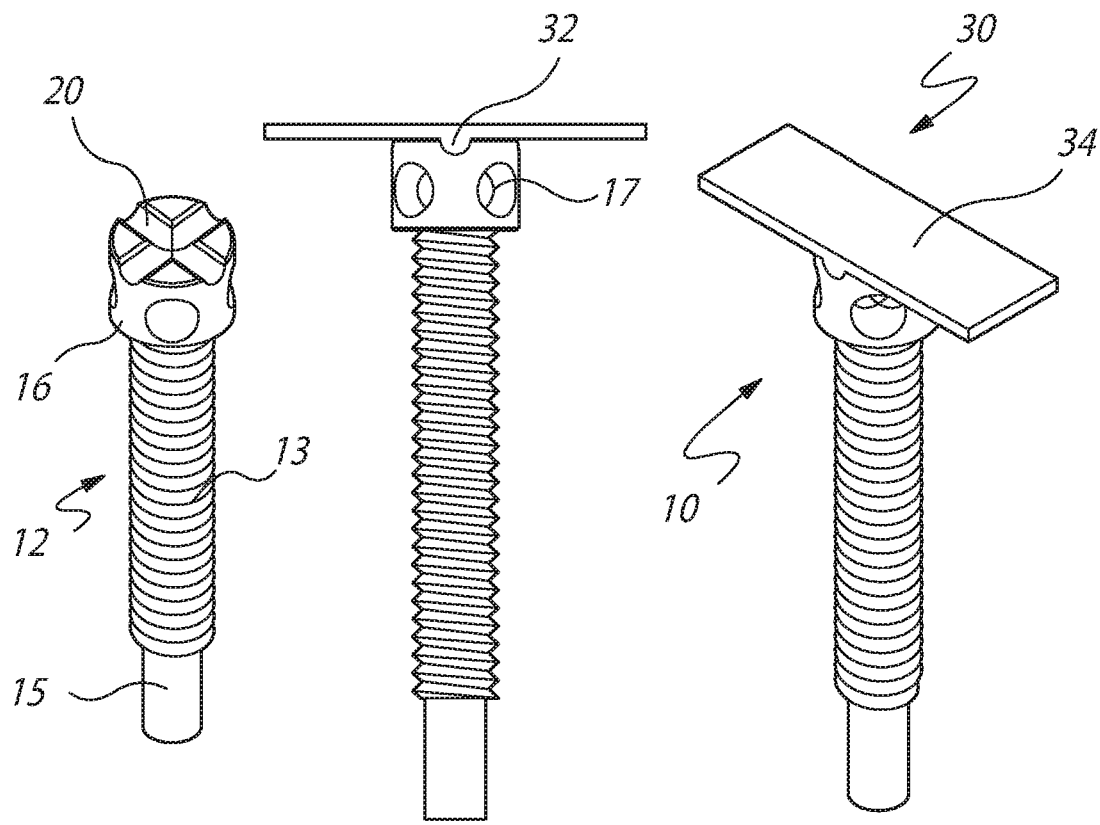
*FIG.2a*     *FIG.2b*     *FIG.2c*

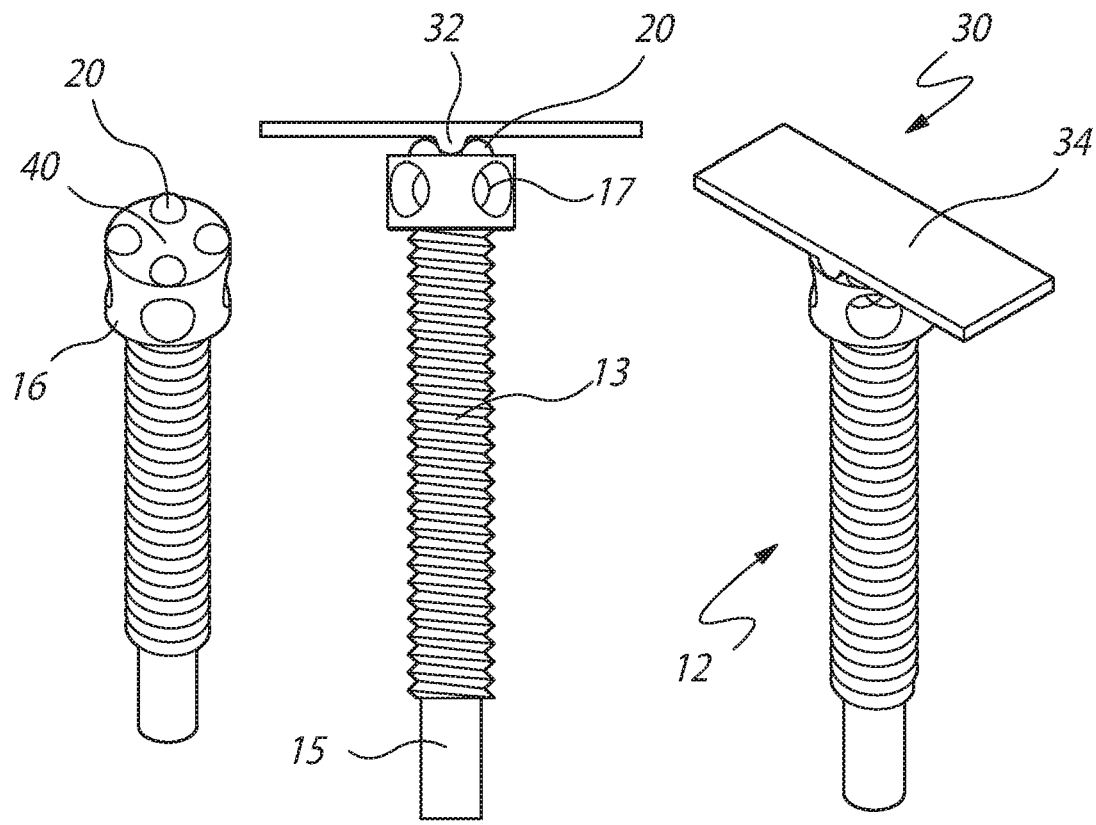
*FIG.3a*   *FIG.3b*   *FIG.3c*

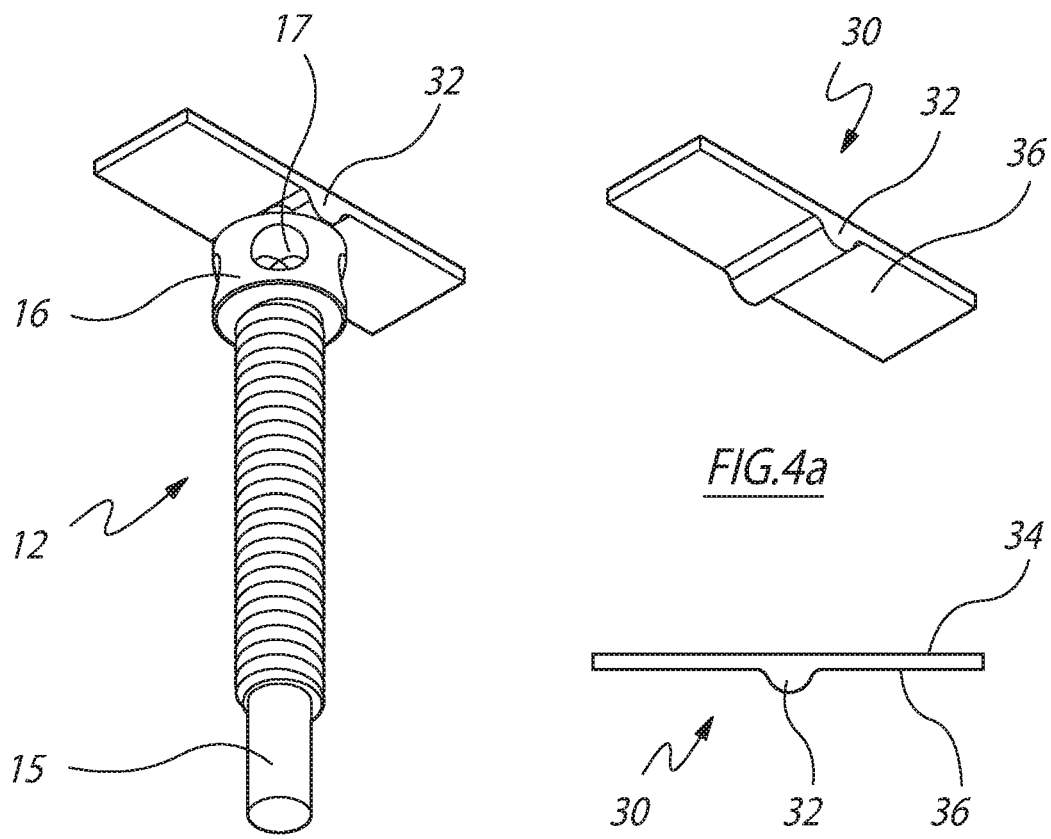
*FIG.3d*
*FIG.4a*
*FIG.4b*
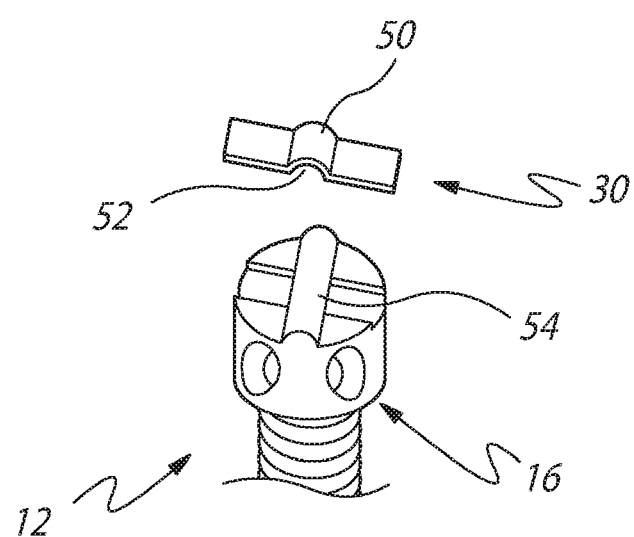
*FIG.5*

LOCKING ASSEMBLY FOR A MEDICAL DEVICE

FIELD

The invention relates to a lock for a medical device. In particular, a screw used with mandibular advancement devices that have application in the treatment of orthodontic conditions, snoring, obstructive sleep apnoea and certain temporomandibular joint disorders. In particular, the invention relates to a locking assembly for such an advancement device.

Although the invention will be described in respect of mandibular advancement devices as an example, the locking assembly could be used on any appropriate medical device. Preferably in respect of that example, it has been well established that snoring and obstructive sleep apnoea and other similar conditions occur where there is at least partial occlusion of the airway and that the tongue is involved in this occlusion. Mandibular advancement devices advance the lower jaw carrying the tongue forward thereby reducing the likelihood of the tongue impacting on the airway.

BACKGROUND

Numerous forms of mandibular advancement devices are known. Once such device by the present applicants is detailed in AU 2005201456. In this document, a mandibular advancement device is described that provides advancement of the lower jaw and permits freedom of the sagittal jaw movement (i.e. jaw opening) while retaining advancement within a range protruded from the reflex or habitual path of closure. Known devices provide an adjustable feature in the form of a plate 1, having an elongate recess 3, a block 5 slidable along the recess 3, the location of the block 5 controlling a degree of mandibular advancement of teeth engaging members 100. Adjustability is provided by a turn buckle mechanism 7 such as a jack screw mechanism or the like, which can be operated by a key, bolt or nut 9 to advance or retract the block 5 as desired along the recess 3 and as shown in FIGS. 1a and 1b. In this way, specialised treatment can be provided by a clinician for each individual user.

In existing systems, it has been found that the key, bolt or nut 9 loosens or "winds back" over time. Such wind back causes loss of protrusion, leading to decrease in treatment efficiency.

A number of unsuccessful devices have attempted to solve this problem by the use of a nut-to-lock screw combination. However, this decreases the effective range of the screw due to the use of the nut 9. There has also been attempted an interference fit at the end of the nut 9, however, this requires very tight tolerances and is expensive. Resistance is also susceptible to wear, thus decreasing over time. These methods and devices are also always under load, which is not favourable for wear resistance.

Accordingly there is a need for a cap that provides mechanical interference with a screw head to prevent the screw loosening on a mandibular appliance, whilst providing an added benefit of tactile feedback to the user.

SUMMARY

It is an object of the present invention to substantially overcome, or at least ameliorate one or more of the disadvantages of existing arrangements, or at least provide a useful alternative to the existing arrangements.

There is disclosed herein a locking assembly for a medical device, the device adapted to adjust the position of an upper teeth engagement member to a lower teeth engagement member, the device having a plate, an elongate recess and a block slidable along said recess to adjust the position of the members relative to each other;
the locking assembly including:
a screw having an elongate shaft having a thread extending substantially towards one end and a head at the other end, the thread adapted to engage the block, the head having at least one engagement member; and
a cap having a corresponding at least one engagement member in use to lock the engagement members together to inhibit said screw from rotating in said block.

Preferably, the head engagement member includes at least one depression.

Preferably, the cap engagement member includes at least one protrusion corresponding to and engageable with said at least one depression.

Preferably, the depression is a channel crossing said head.

Preferably, the head engagement member includes at least one protrusion extending from said head.

Preferably, the cap engagement member includes at least one depression corresponding to and engageable with said at least one protrusion.

Preferably, the cap is an elongate plate having a top surface and a bottom surface, the plate including the at least one engagement member on the bottom surface.

Preferably, the cap is manufactured of a rigid and hard wearing material.

Preferably, the cap may be formed of a polymeric material such as PMMA that envelopes the plate as part of a larger assembly.

Alternatively, the cap may be formed of a metal, whereby the cap is welded to the medical device.

In another embodiment, there is disclosed a locking assembly including:
a screw having an elongate shaft having a thread extending substantially towards one end and a head at the other end, the thread adapted to engage a medical device, the head having at least one engagement member; and
a cap having a corresponding at least one engagement member in use to lock the engagement members together to inhibit said screw from rotating in said medical device.

In another embodiment, the block that is slidable along the recess is connected directly or indirectly to a protuberance such that it achieves advancement of the oral appliance.

In another embodiment, the plate has at least one engagement member that corresponds to at least one engagement member on the screw head to lock the engagement members together to inhibit the screw from rotating in the medical device.

BRIEF DESCRIPTION OF THE DRAWINGS

FIGS. 2a, 2b, 2c and 2d show a screw and cap of an embodiment of the present invention;

FIGS. 3a, 3b, 3c and 3d show a screw and cap of another embodiment of the present invention;

FIGS. 4a, 4b show a cap of an embodiment of the present invention; and

FIG. 5 shows a cap and screw of another embodiment of the present invention.

DETAILED DESCRIPTION OF THE EMBODIMENTS

Figure 1A:
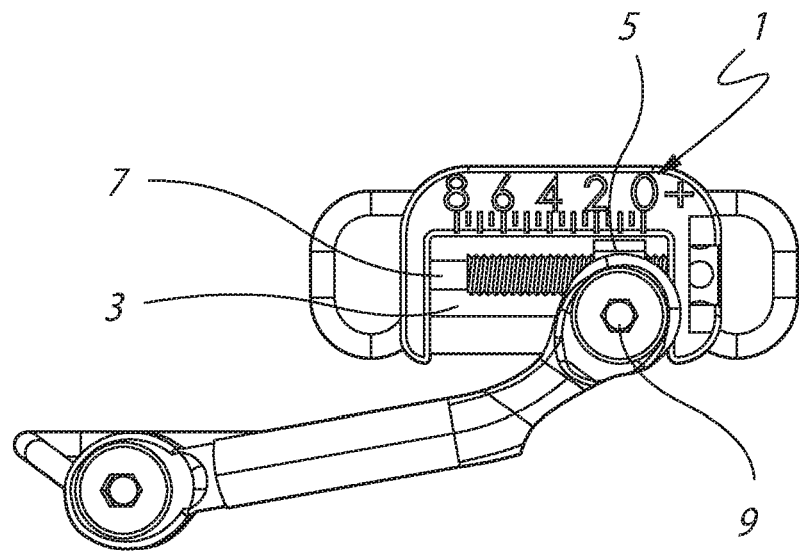
FIGS. 1a and 1b show an adjustment device of the prior art.
Figure 1B:
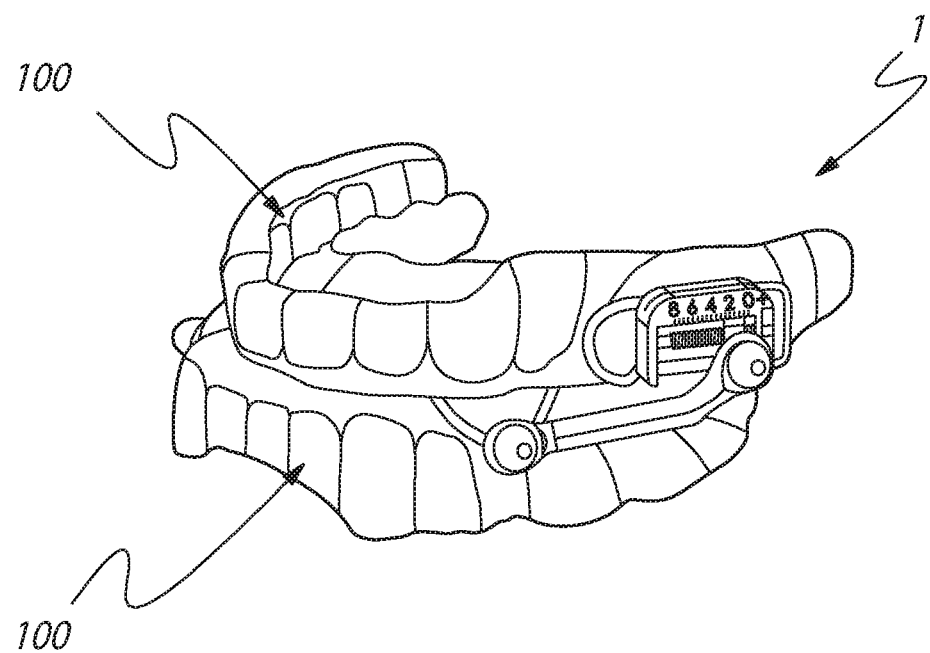

FIGS. 1a and 1b show a prior art medical device.

In FIGS. from 2a to 7, there is schematically depicted embodiments of the present invention in various forms. There is disclosed a locking assembly 10 for a medical device 1. As mentioned previously, the medical device 1 could be any type of suitable medical device. The assembly 10 includes a screw 12 (as best seen in FIG. 2a—also turnbuckle 7) having a thread 13 extending substantially towards one end 15 which may or may not have a thread extending to the end. The unthreaded end 15 enables the screw 12 to rotate freely without shifting. The thread 13 may be any type of thread. A head 16 is located at the other end. The head 16 may be of any shape or size, and may or may not have holes 17 to assist with screwing the screw 12 into the medical device 1. By way of example, the head 16 may be have a hexagon shape which may be turned using a mini wrench. The thread 13 is adapted to engage part of the medical device 1 in use. In the example shown in FIG. 1, the screw 13 would engage the block 5. The head 16 includes at least one engagement member 20. In FIG. 2a, there are two engagement members 20 shown, each being a channel and crossing across the head 16. It will however be appreciated that other types of channels 20 or depressions could be utilised.

The assembly 10 further includes a cap 30 having at least one engagement member 32 corresponding with the depressions or channels 20, and adapted in use to lock with the depressions or channels 20 to lock the head 16 and cap 30 together to inhibit the screw 12 from rotating in the medical device 1 (for example, in the block 5). It will be understood that the rotation of the screw 12 in the medical device 1 may be undesirable in preferred applications. For example, the screw 12 mechanism of the medical device 1 may need to be able to function as a turnbuckle (e.g. turnbuckle 7 as discussed above). This locking mechanism may therefore generate sufficient resistance to minimise or altogether prevent undesired rotation or movement. The cap 30 may be manufactured from a rigid and hard-wearing material such as a metal (e.g. stainless steel), or a polymeric material such as PEEK or polyamide.

Figure 2D:
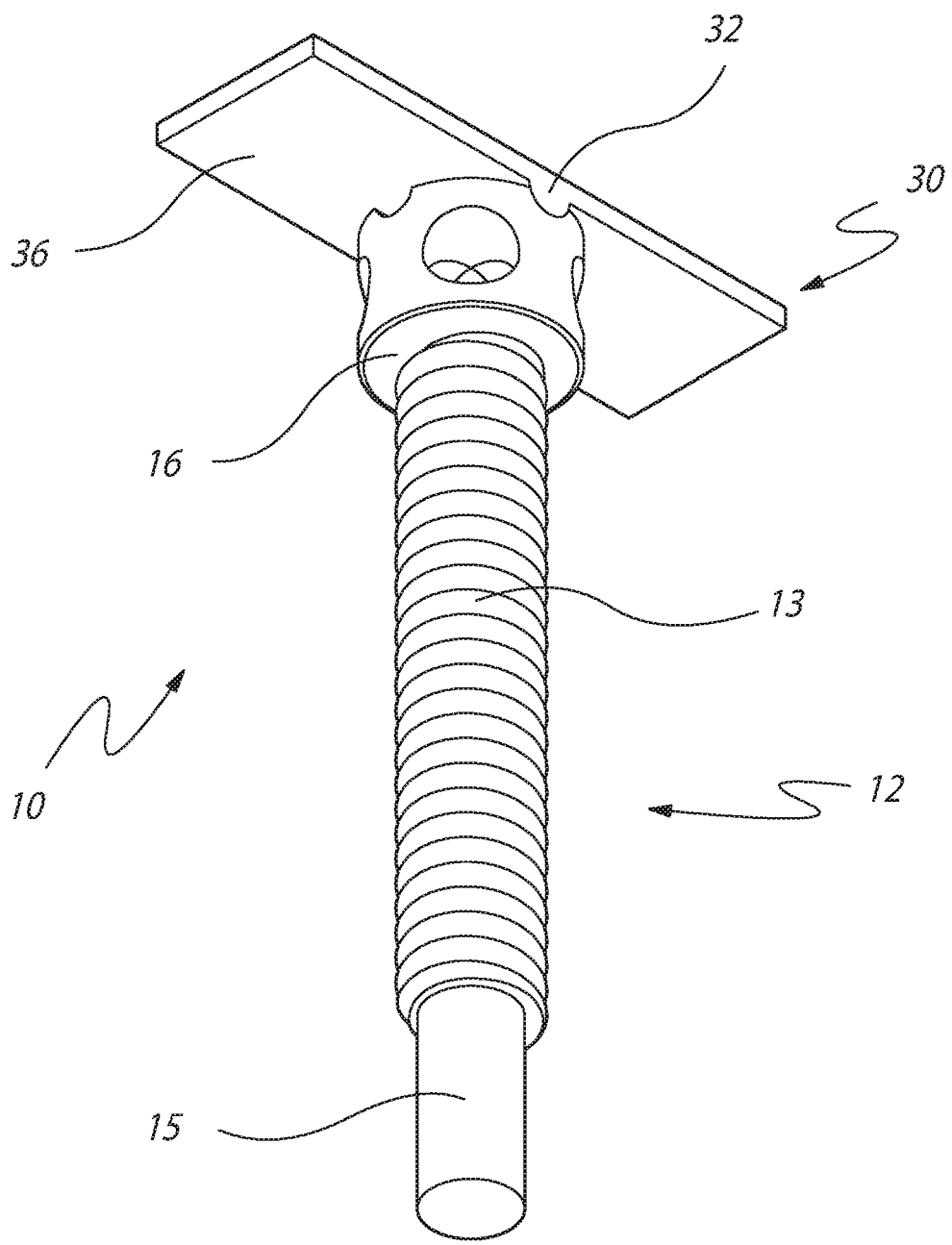

In the embodiment shown in FIGS. 2b, 2c and 2d, the cap 30 is an elongate plate having a top surface 34 and a bottom surface 36. The at least one engagement member 32 takes the form of a protrusion extending along the length of the underside 36 of the cap 30 to engage with the at least one channel 20 of the head 16. In the embodiments shown in FIGS. 3a, 3b, 3c and 3d, the at least one engagement member 20 of the head 16 are protrusions (bumps) extending away from a top surface 40 of the head 16. In this case, the protrusions are in the shape of balls or spheres, however, it will be appreciated that the protrusions could be any particular shape.

The engagement member (protrusion) 32 of the cap (plate) 30 (as shown in FIGS. 4a and 4b) includes a ridge extending along the underside 36 of the cap 30. The ridge fits between and engages the protrusions 20 of the head 16. It will be appreciated that various shapes of engagement members 20, 32 could be utilised to effect the locking between the cap 30 and the head 16 of the screw 12, as long as they are complimentary male and female (positive and negative) shapes.

In FIG. 5, a further embodiment is shown in which the cap 30 is not flat and includes a raised section 50 and depressed section 52 which compliment raised ridges 54 on the head 16 of the screw 12. A reverse arrangement could also be utilised. The cap 30 may be formed of a metal such as stainless steel, or a polymeric material such as PMMA that envelopes the plate as part of a larger assembly. The cap 30 may also be welded or fixed to the device 1.

Figure 6:
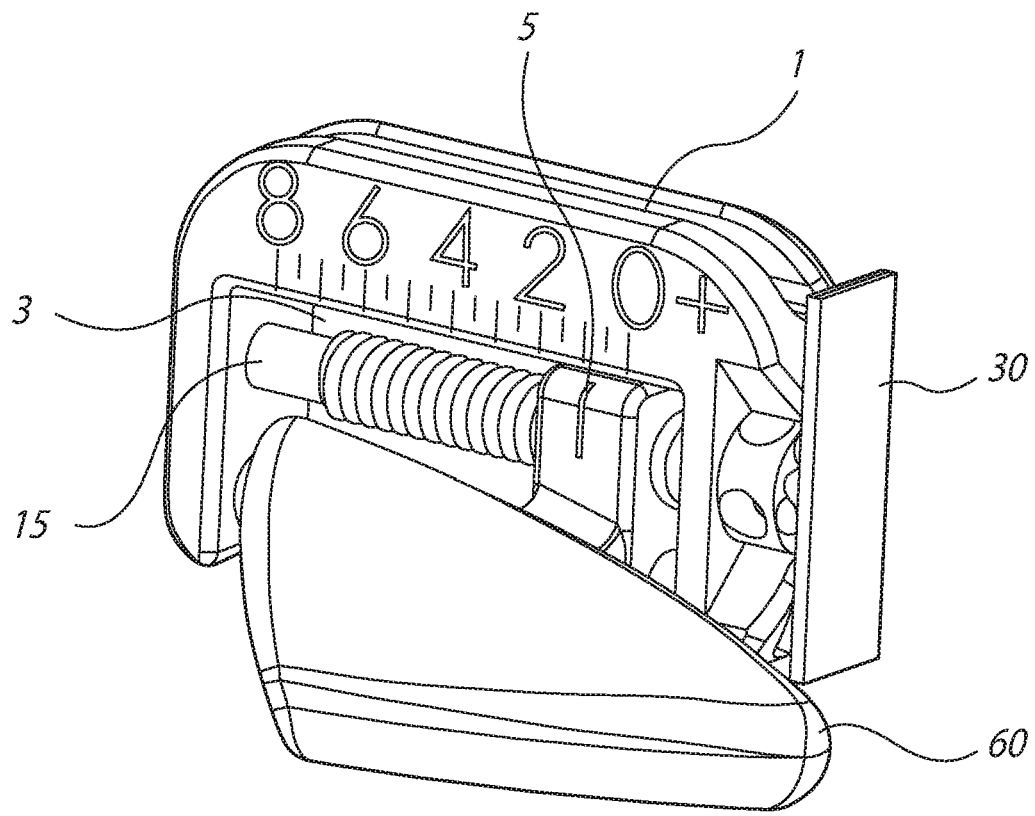
FIG. 6 shows another embodiment of the present invention where the slidable block has a functional protuberance.

In FIG. 6, the block 5 that is slidable along the recess 3 is connected directly or indirectly to a protuberance 60 such that advancement of the oral appliance may be achieved.

Figure 7:
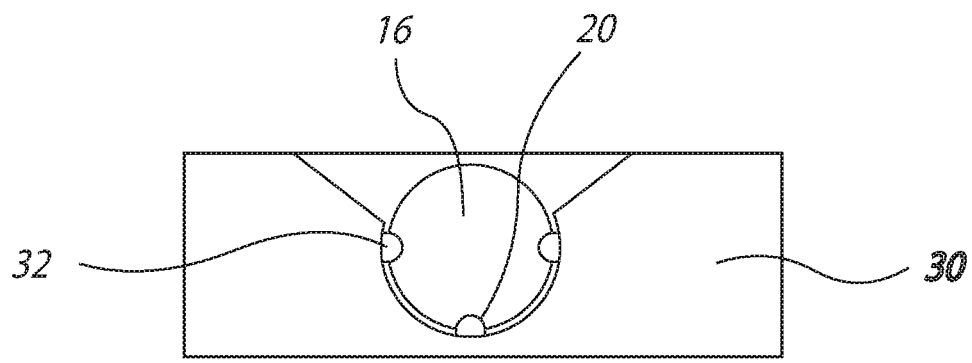
FIG. 7 shows another embodiment of the invention.

In FIG. 7, the plate 30 has at least one engagement member 32 that corresponds to at least one engagement member 20 on the screw head 16, such that the corresponding engagement members may be locked together to inhibit the screw 12 from rotating in the medical device 1. The engagement occurs at the radial surface of the head 16. The plate 30 feature may be fixed, or alternatively be integrated into, the design of the medical device 1.

The present invention at least in a preferred embodiment provides a locking assembly 10 to prevent a screw 12 from loosening. The cap 30 provides a mechanical interference with the screw head 16 to prevent the screw 12 from loosening. The mechanical interference provided by the screw head 16 and cap 30 is not susceptible to wear over time. The prior art devices rely on friction applied at the screw head 16 to prevent "wind back", which results in loss of resistance over time with continued use. The prior art devices are under load at all times which increases damage to the cap 30 as compared to the present invention. Resistance is only applied when the screw head 16 is rotated. This arrangement may at least improve long term resistance to wind back.

The present invention at least in a preferred embodiment may also provide tactile feedback to a user during rotation as the positive/negative shapes engage one another. Further, some prior art devices require at least two keys to lock and unlock the screw 12. This invention at least in a preferred embodiment may provide only one key, in the form of the cap 30. The present invention in a preferred embodiment does not require tight tolerance fits between the screw 12 and cap 30. Further, the screw 12 can be any length. In an alternate embodiment, the cap 30 could also have means to engage with the holes 17 in the head 16 for further locking. It should also be appreciated that the locking assembly of the embodiments of the present invention works in a single plane of the cap 30 unlike the prior art.

Although the invention has been described with reference to a preferred embodiment, it will be appreciated by those persons skilled in the art that the invention may be embodied in many other forms.

The invention claimed is:

1. A locking assembly for a medical device, the device adapted to adjust the position of an upper teeth engagement member to a lower teeth engagement member, the device having a plate, an elongate recess and a block slidable along said recess to adjust the position of the members relative to each other;

the locking assembly including:

a screw having an elongate shaft having a thread extending substantially towards one end and a head at the other end, the thread adapted to engage the block, the head having at least one engagement member; and a cap having a corresponding at least one engagement member in use to lock the engagement members together to inhibit said screw from rotating in said block, wherein the cap is an elongate plate having a top surface and a bottom surface, the plate including the at least one engagement member on the bottom surface.

2. The locking assembly of claim 1, wherein the head engagement member includes at least one depression.

3. The locking assembly of claim 2, wherein the cap engagement member includes at least one protrusion corresponding to and engageable with said at least one depression.

4. The locking assembly of claim 1, wherein the depression is a channel crossing said head.

5. The locking assembly of claim 1, wherein the head engagement member includes at least one protrusion extending from said head.

6. The locking assembly of claim 5, wherein the cap engagement member includes at least one depression corresponding to and engageable with said at least one protrusion.

7. The locking assembly of claim 1, wherein the cap is manufactured of a rigid and hard wearing material.

8. The locking assembly of claim 1, wherein the cap is formed of a polymeric material such as PMMA that envelopes the plate as part of a larger assembly.

9. The locking assembly of claim 1, wherein the cap is formed of a metal, whereby the cap is welded to the medical device.

10. The locking assembly of claim 1, wherein the block that is slidable along the recess is connected directly or indirectly to a protuberance such that it achieves advancement of the oral appliance.

11. The locking assembly of claim 1, wherein the plate has at least one engagement member that corresponds to at least one engagement member on the screw head to lock the engagement members together to inhibit the screw from rotating in the medical device.

12. A locking assembly including:

a screw having an elongate shaft having a thread extending substantially towards one end and a head at the other end, the thread adapted to engage a medical device, the head having at least one engagement member; and a cap having a corresponding at least one engagement member in use to lock the engagement members together to inhibit said screw from rotating in said medical device, wherein the cap is an elongate plate having a top surface and a bottom surface, the plate including the at least one engagement member on the bottom surface.

* * * * *